United States Patent [19]

Misra

[11] Patent Number: 4,714,714
[45] Date of Patent: Dec. 22, 1987

[54] ARACHIDONIC ACID ANALOGS

[75] Inventor: Raj N. Misra, Princeton, N.J.

[73] Assignee: E. R. Squibb & Sons, Inc., Princeton, N.J.

[21] Appl. No.: 837,241

[22] Filed: Mar. 7, 1986

Related U.S. Application Data

[62] Division of Ser. No. 638,335, Aug. 6, 1984, Pat. No. 4,599,439.

[51] Int. Cl.$^4$ .................... C07C 61/35; A61K 31/19
[52] U.S. Cl. .................... 514/572; 514/729; 562/506; 568/700
[58] Field of Search .................... 560/124; 568/700; 514/531, 729, 572; 562/506

[56] References Cited

U.S. PATENT DOCUMENTS 4,442,099  4/1984  Nicolaou .................... 560/124

OTHER PUBLICATIONS

Corey, Tetrahedron Letters, 24, pp. 265–268 (1983).

Primary Examiner—Michael L. Shippen
Attorney, Agent, or Firm—Lawrence S. Levinson; Burton Rodney

[57] ABSTRACT

Analogs of arachidonic acid are provided having the structure

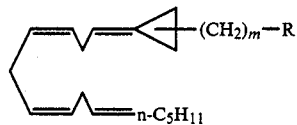

wherein R is $CH_2OH$ or $CO_2H$ and m is 1 or 2. These compounds are useful as inhibitors of leukotriene and prostaglandin biosynthesis and as such are useful an antiallergy and antiinflammatory agents.

14 Claims, No Drawings

ARACHIDONIC ACID ANALOGS

This is a division of application Ser. No. 638,335, filed Aug. 6, 1984, now U.S. Pat. No. 4,599,439.

DESCRIPTION OF THE INVENTION

The present invention relates to analogs of arachidonic acid which are inhibitors of prostaglandin and leukotriene biosynthesis and as such are useful, for example, as anti-allergy and antiinflammatory agents. These compounds have the structural formula

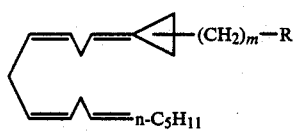
I wherein R is $CH_2OH$ or $CO_2H$ and m is 1 or 2. Compounds of formula I wherein R is $CH_2OH$ serve as intermediates for preparing the final products of the invention wherein R is $CO_2H$.

Preferred compounds of the invention have the following structures:

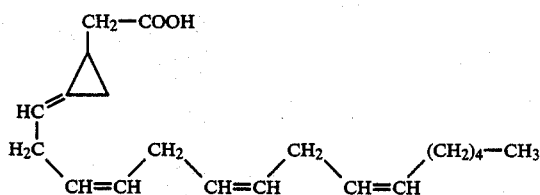
IA

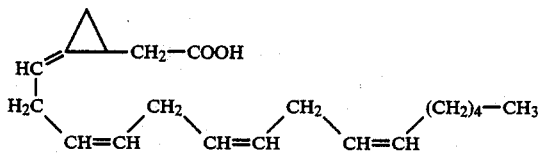
IB

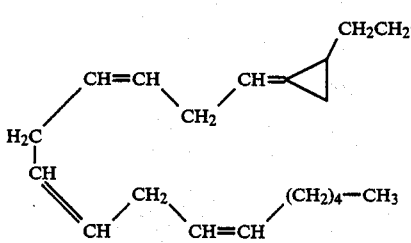
IC

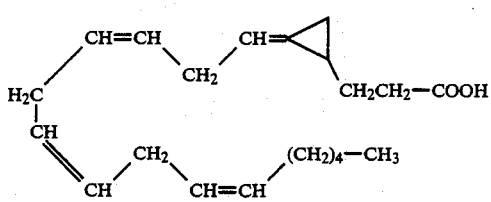
ID

In addition, in accordance with the present invention, several novel intermediates are provided as detailed below which are formed during the procedure for preparing compounds of formula I.

One such novel intermediate is the aldehyde

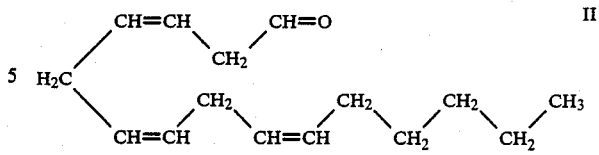
II which has the name (Z,Z,Z)-3,6,9-pentadecatrienal.

Other novel intermediates formed during the preparation of the compounds of formula I having the following formulae

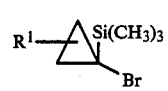
III wherein $R^1$ is $(CH_2)_q$—CH=$CH_2$ wherein q is 0 or 2, or $R^1$ is $(CH_2)_p$—$OR^2$ wherein $R^2$ is H or $Si(C_6H_5)_2$-$C(CH_3)_3$ and p is 2 or 3

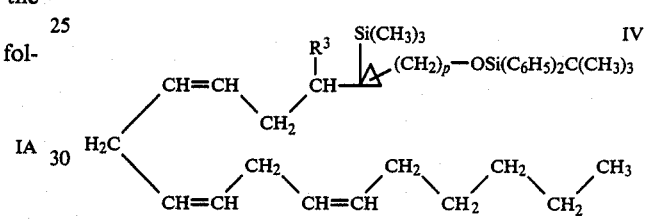
IV wherein $R^3$ is Cl or OH and p is 2 or 3.

The above formulae I, II and III represent all possible stereoisomers.

The compounds of the formula I of the invention may be prepared as outlined below.

To prepare compounds of the invention wherein m is 2, a slurry of potassium t-butoxide in 1,5-hexadiene A

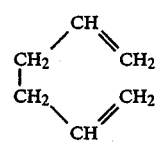
A is cooled to from about −10° to about −25° C. and added is a solution of bromoform ($CHBr_3$) in 1,5-hexadiene. The reaction is stirred while maintaining a reduced temperature of −20° to 0° to form the dibromide B

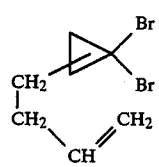
B

The dibromide B is then subjected to a metalation reaction wherein B is treated with n-butyllithium in the presence of tetreahydrofuran at reduced temperatures of −90° to −95° C. to form the anion C

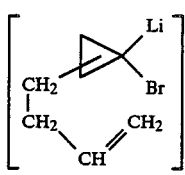

C

The anion C, without separation from the reaction mixture, is then made to undergo silylation wherein C is treated with chlorotrimethylsilane ((CH$_3$)$_3$SiCl) while maintaining the reaction at reduced temperatures of from about −95° to about 75° C. to form the bromosilane IIIA which is a novel intermediate and forms a part of the present invention

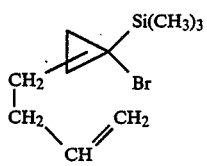

IIIA

The bromosilane IIIA is next made to undergo ozonolysis of the double bond by treating IIIA in an anhydrous solvent such as methanol with ozone to form the ozonide D

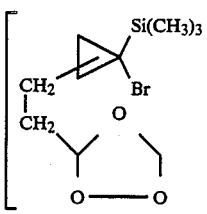

D which, without separation from the reaction mixture, is reacted with sodium borohydride to form the alcohol IIIB which itself is a novel intermediate and forms part of the present invention

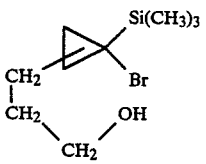

IIIB

Next, the alcohol portion of IIIB is protected by reacting IIIB with t-butylchlorodiphenylsilane in the presence of triethylamine and 4-dimethylaminopyridine to form the protected compound IIIC which itself is novel and forms a part of the present invention

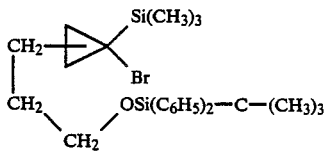

IIIC

The protected compound IIIC is then metalated by reaction of a solution of IIIC in tetrahydrofuran with n-butyllithium at reduced temperatures of from about −70° to about −85° C. to form intermediate E

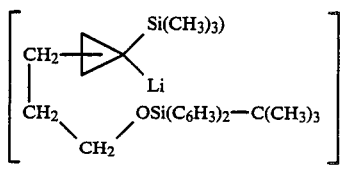

E which, without separation from the reaction mixture, is reacted with the aldehyde II dissolved in ether

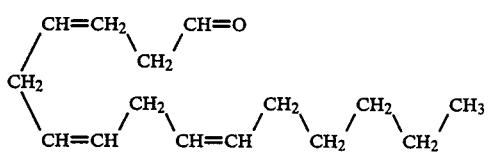

II to form the β-hydroxysilane IVA (in the form of a mixture of diastereomers) which, itself, is novel and forms a part of the present invention

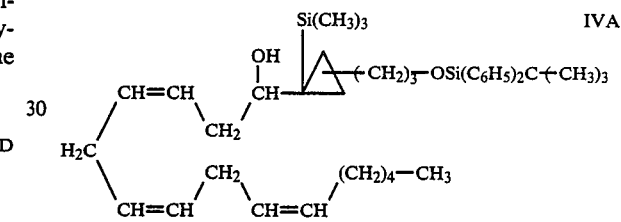

IVA

Depending upon which isomeric form of the final product is desired, the appropriate β-hydroxysilane diastereomer (obtained from the reaction mixture by conventional separation techniques) in methylene chloride is then reacted with thionyl chloride in the presence of triethylamine to form the β-chlorosilane IVB which, itself, is novel and forms part of the present invention

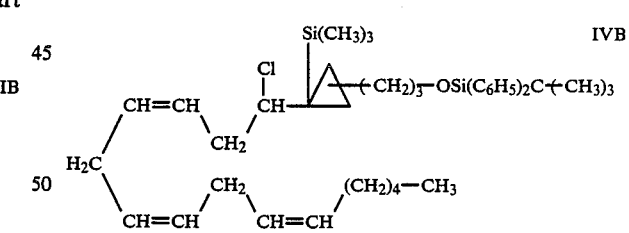

IVB which is then made to undergo a Peterson olefination and deprotection by reacting IVB in the presence of dimethyl sulfoxide with tetra-n-butylaxmmonium fluoride to form the alcohol IE

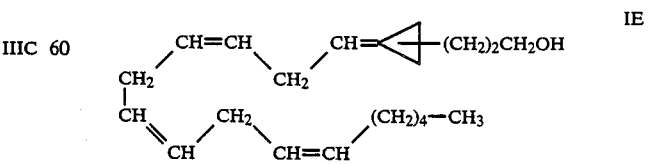

IE

Alcohol IE is then made to undergo a Jones oxidation by reacting IE in acetone with Jones reagent (H$_2$CrO$_4$) to form the acid IF

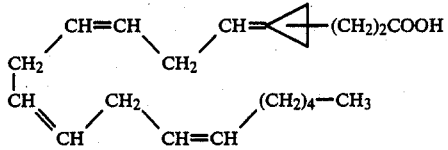

IF which includes all stereoisomers. The particular stereoisomer obtained will be determined by the particular β-hydroxysilane diastereomer IVA employed in the above-described reaction sequence.

To form compounds of formula I of the invention wherein m is 1, the bromosilane II is made to undergo a hydroboration-oxidation reaction sequence by reacting III (wherein q is CH=CH) in tetrahydrofuran with borane-tetrahydrofuran complex. Without isolation the intermediate borane formed is treated with basic hydrogen peroxide to form the alcohol IIID

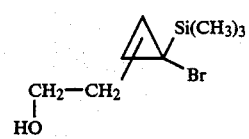

IIID

The alcohol IIID is then protected as described hereinbefore to form the novel protected alcohol IIIE

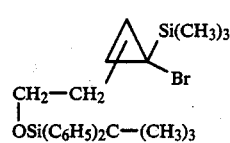

IIIE which is then metalated with n-butyllithium as described above and then reacted with aldehyde II as described above to form the novel β-hydroxysilane IVC (in the form of a mixture of diastereomers)

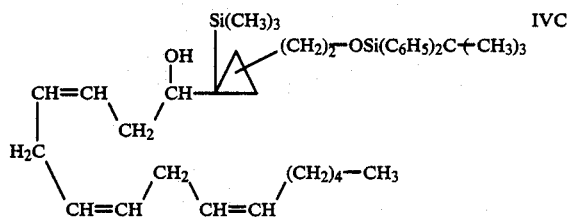

IVC

The appropriate β-hydroxysilane diastereomer is then made to undergo a chorination reaction by reaction with thionyl chloride as described above to form the corresponding novel β-chlorosilane IVD

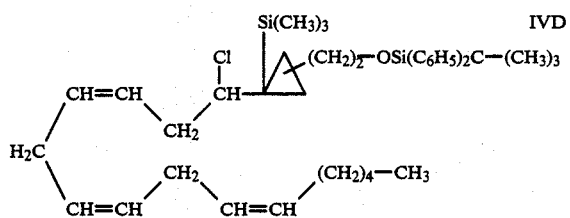

IVD which is then made to undergo a Peterson olefination and alcohol deprotection as described above to form the alcohol IG

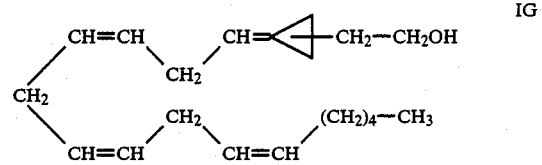

IG

Alcohol IG is then subjected to a Jones oxidation as described above to form the acid IH

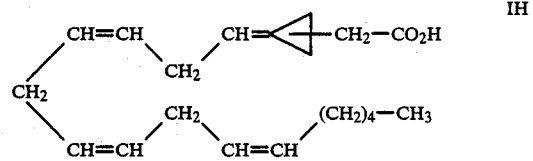

IH which includes all stereoisomers. The particular stereoisomer obtained will be determined by the particular β-hydroxysilane diastereomer IVC employed in the above described reaction sequence.

The novel intermediate aldehyde II may be prepared by subjecting arachidonic acid

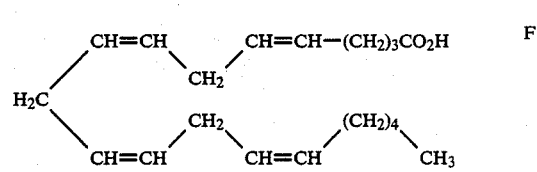

F to an iodolactonization reaction wherein arachidonic acid is reacted with potassium iodide to form the iodolactone G

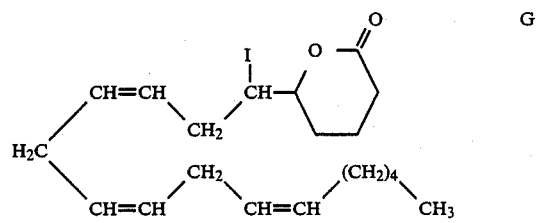

G which is then saponified by treatment with lithium hydroxide to form the epoxy compound H

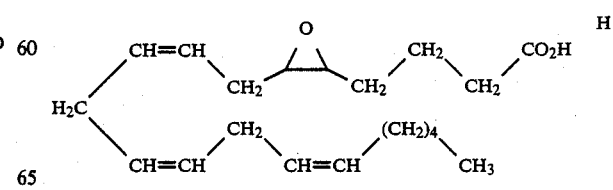

H which is treated with diazomethane to form the ester J

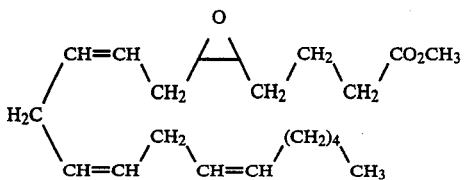

Ester J is then made to undergo oxidative cleavage by reaction with periodic acid (H₅IO₆) in anhydrous ether to form the aldehyde II.

The compounds of the invention prevent prostaglandin and leukotriene C₄ formation in macrophages (Samuelsson, B., Science, Vol. 220, p. 568–575, 1983). The administration of compounds of this invention to humans or animals provides a method for treating allergy of a reagin or non-reagin nature. Asthma is preferably treated but any allergy wherein leukotrienes are thought to be involved as pharmacological mediators of anaphylaxis can be treated. For example, the compounds of this invention can be used for treatment of such conditions as allergic rhinitis, food allergy and urticaria as well as asthma. In addition, the compounds of the invention are useful as antiinflammatory agents in the manner of indomethacin and phenylbutazone as indicated by carragenin-induced edema in the rat [Ref: Winter et al, J. Pharmacol, Exp. Ther. 141:369, 1963] and they may be used to decrease joint swelling, tenderness, pain and stiffness in conditions such as rheumatoid arthritis.

An effective but essentially non-toxic quantity of the compound is employed in treatment.

The compounds of the invention can be administered orally or parenterally to various mammalian species known to be subject to such maladies, e.g., humans, cats, dogs, and the like in an effective amount within the dosage range of about 1 to 100 mg/kg, preferably about 1 to 50 mg/kg and especially about 2 to 25 mg/kg on a regimen in single or 2 to 4 divided daily doses.

The active substance can be utilized in a composition such as tablet, capsule, solution or suspension containing about 5 to about 500 mg per unit of dosage of a compound or mixture of compounds of formula I. They may be compounded in conventional matter with a physiologically acceptable vehicle or carrier, excipient, binder, preservative, stabilizer, flavor, etc. as called for by accepted pharmaceutical practice. Also as indicated in the discussion above, certain members additionally serve as intermediates for other members of the group.

The following Examples represent preferred embodiments of the present invention. Unless otherwise indicated, all temperatures are expressed in degrees Centigrade. TLC plates were visualized by spraying and heating with 5% phosphomolybdic acid in ethanol.

EXAMPLE 1

(Z,Z,Z,Z)-2-(3,6,9-Pentadecatrienylidene)cyclopropane-propanoic acid

A. (Z,Z,Z)-3,6,9-Pentadecatrienal (1)
(Z,Z,Z)-6-(1-Iodo-3,6,9-pentadecatrienyl)-γ-valerolactone The procedure of E. J. Corey, et al., JACS, 101, 1586 (1979) was followed.

To a solution of 450 mg (1.48 mmol) of arachidonic acid in 30 ml of 2:1 (V:V) THF/H₂O was added 740 mg (7.40 mmol) of potassium bicarbonate, then 2.00 g (12.0 mmol) of neutral potassium iodide. The mixture was stirred for 10 minutes until homogeneous, cooled to 0°, then 5.65 g (22.2 mmol) of iodine was added in one portion. The reaction mixture was stirred at 0° for 3.5 hours, then added to 50 ml of ether. The dark solution was washed with two 75 ml portions of ice-cold 5% aqueous sodium bisulfite until colorless, then washed with 50 ml of saturated aqueous NaHCO₃ and 50 ml of H₂O and dried (MgSO₄) and concentrated in vacuo to afford 704 mg of crude title iodo-lactone as a pale yellow oil.

TLC (1:19 MeOH/CH₂Cl₂) R$_f$=0.84, PMA and UV.

(2) 5,6-Epoxy arachidonic acid, methyl ester

To a solution of the crude iodo-lactone in 10 ml of 3:2 (V:V) THF/H₂O was added 160 mg (3.81 mmol) of lithium hydroxide monohydrate. The reaction mixture was stirred at 25° for 4 hours then cooled to 0° and glacial HOAc was added dropwise until pH=6. To the resulting solution was added ethereal diazomethane (prepared from 1.0 g 1-methyl-3-nitro-1-nitroso-guanidine, MNNG, Fieser & Fieser, Vol. I (1967), p. 192) until a bright yellow color persisted. After 5 minutes the excess diazomethane was quenched by dropwise addition of glacial HOAc until the reaction mixture was colorless. The resulting solution was added to 25 ml of saturated aqueous NaHCO₃ and extracted with two 25 ml portions of ether. The combined ether extracts were dried (MgSO₄), concentrated in vacuo and the resulting crude oil purified by flash chromatography (15×3.0 cm, silica gel, 1:5 ether/pet ether) to afford 341 mg (69%) of title epoxy ester as a pale yellow, foul-smelling oil.

IR (film) 3.45, 5.74, 6.98, 8.03, 8.58 μ.
400 MHZ ¹H NMR(CDCl₃) δ0.89 (t, 3H), 1.22–1.32 (m, 6H), 1.50–1.69 (m, 2H), 1.75–1.93 (m, 2H), 2.05 (q, J=7, 2H), 2.17–2.28 (m, 1H), 2.32–2.50 (m, 3H), 2.82 (dt, J=7, 11 Hz, 4H) 2.91–2.98 (m, 2H) 3.69 (s, 3H) 5.26–5.60 (m, 6H)
MS (CI): 335 (MH³⁰), 3.17, 303, 285, 191, 177.
TLC: R$_f$(1:4 ether/petroleum ether)=0.32, PMA.

(3) (Z,Z,Z)-3,6,9-Pentadecatrienal

A mixture of 570 mg (2.50 mmol) of periodic acid crystals in 65 ml of anhydrous ether was stirred rapidly for 1 hour until nearly homogeneous, then a solution of 840 mg (2.51 mmol) of Part (2) epoxy ester in 5 ml of ether was added in one portion at room temperature. The reaction mixture was stirred for 1 hour and then filtered. The filtrate was concentrated in vacuo and the resulting crude oil was purified by flash chromatography (12×3.0 cm, silica gel, 1:19 EtOAc/petroleum ether) to afford 360 mg (66%) of title aldehyde as a pale yellow oil.

IR (film) 3.44, 3.70 (w), 5.79; 5.92, 6.84, 7.25 μ.
60 MHz ¹H NMR(CDCl₃) δ 6 0.90 (cr t, 3H), 1.33 (br, 6H), 1.80–2.33 (br, 2H), 2.82(m, 4H), 3.23 (cr dd, J=2,6 Hz, 2H), 5.07–5. 87 (m, 6H), 9.73 (m, 1H),
MS (CI): 221 (MH+), 220, 203, 177, 137, 133.
TLC: R$_f$(1:5 EtOAc/petroleum ether)=0.52, PMA.

B. 1,1-Dibromo-2-but-3-enylcyclopropane

To a rapidly stirred slurry of 4.70 g (42.0 mmol) of potassium tert-butoxide in 50 ml of 1,5-hexadiene cooled to −20° was added dropwise a solution of 3.7 ml (42 mmol) of bromoform in 5 ml of 1,5-hexadiene over 15 minutes. The reaction mixture was stirred at −20° for 30 minutes then at 0° for 60 minutes followed by addition to 50 ml of 1M aqueous HCl solution. The organic layer was separated, washed with 100 ml of H₂O, dried (MgSO₄), concentrated in vacuo and evaporatively distilled (40°–45°, 0.1 mm) to afford 7.40 g (69%) of title dibromide as a pale yellow liquid.

60 MHz $^1$H NMR(CDCl₃) δ1.03–2.00 (m, 5H), 2.00–2.57 (m, 2H), 4.80–5.30 (m, 2H), 5.47–6.27 (m, 1H),

15 MHz $^{13}$C NMR(CDCl₃) δ28.4, 29.0, 30.7, 32.0, 32.3, 115.4, 137.2. MS (CI); 257, 255, 175, 173

C. 1-Bromo-2-but-3-enyl-1-trimethylsilylcyclopropane

To a solution of 1.41 g (5.55 mmol) of Part B dibromide in 10 ml of THF and 3.0 ml of ether cooled to −95° was added 2.3 ml (2.6 M in hexane, 6.0 mmol) of n-butyllithium dropwise maintaining the reaction mixture temperature between −95° to −90°. The solution was stirred at this temperature for 1 hour, then 0.80 ml (6.3 mmol) of chlorotrimethylsilane was added dropwise. The resulting solution was stirred at −95° for 1 hour, then at −78° for 1 hour, followed by warming to room temperature and quenching with H₂O. The reaction mixture was added to 30 ml of H₂O and extracted with two 15 ml portions of petroleum ether. The combined organic extracts were dried (MgSO₄) and concentrated in vacuo to afford 924 mg (67%) of crude bromosilane as a pale yellow liquid.

60 MHz $^1$H NMR(CDCl₃) δ 0.15 (s, 6H), 0.50–2.47 (m, 7H)), 4.77–5.27 (m, 2H), 5.47–6.27 (m, 1H).

D. 2-Bromo-2-(trimethylsilyl)cyclopropanepropanol

A solution of 810 mg (3.28 mmol) of crude Part C bromosilane in 6.0 ml of anhydrous methanol was cooled to −78° and ozone was rapidly bubbled into the solution until a blue color persisted. The solution was purged with nitrogen then added with stirring in several portions at −78° was a total of 350 mg (9.21 mmol) of sodium borohydride. After 15 minutes the reaction mixture was allowed to warm slowly to room temperature and stirred for 16 hours. The resulting solution was added to 30 ml of 1M aqueous HCl and extracted with three 10 ml portions of ether. The combined organic extracts were dried (MgSO₄), concentrated in vacuo and the resulting crude oil purified by flash chromatography (14×3.0 cm, silica gel, 1:4 EtOAc/petroleum ether) to afford 600 mg (73%) of title alcohol as a colorless oil.

IR (film) 3.02, 3.41, 6.91, 8.03, 9.02, 9.50, 11.95 μ.

60 MHz $^1$H NMR(CDCl₃) δ 0.13 (s, 9H) 0.65 (t, J=6 Hz, 1H) 0.87–2.0 (m, 7H) 3.63 (t, J=6 Hz, 2H)

MS (CI): 253, 251 (MH³⁰), 155, 111, 93, 81. TLC: R_f (1:4 EtOAc/petroleum ether)=0.23, PMA.

E. 1-Bromo-2-[3-[(t-butyldiphenylsilyl)oxy]propyl]-1-(trimethylsilyl)cyclopropane A solution of 1.17 g (4.66 mmol) of title D alcohol, 1.25 g (4.55 mmol) of tert-butylchlorodiphenylsilane, 0.95 ml (6.9 mmol) of sieve-dried triethylamine and 50 mg of 4-dimethylaminopyridine in 10 ml of dry CH₂Cl₂ was stirred at room temperature for 18 hours. The reaction mixture was added to 20 ml of ice-cold 1M aqueous HCl solution and extracted with 20 ml of petroleum ether. The organic extract was washed with 10 ml of saturated NaHCO₃ solution, dried (MgSO₄), concentrated in vacuo and the resulting crude oil was purified by flash chromatography (12×5.0 cm, silica gel, 1:6 EtOAc/petroleum ether) to yield 2.14 g (96%) of protected alcohol as a pale yellow oil.

IR (film) 3.40, 6.80, 7.03, 7.22, 8.04, 9.05, 11.97, 13.60, 14.36 μ.

60 MHz $^1$H NMR(CDCl₃) δ 0.17 (s, 9H), 0.47–1.97 (m, 16H with 9H, singlet at δ 1.05), 3.67 (t J=6 Hz, 2H), 7.17–7.83 (m, 10H).

TLC: R_f (1:4 EtOAc/petroleum ether)=0.83, PMA and UV.

F. 1-[2-[3-[t(Butyldiphenylsilyl)oxy]propyl]-1-(trimethylsilyl)cyclopropyl]-3,6,9-pentadecatrien-1-ol (Diastereomer F)

G. 1-[2-[3-[(t-Butyldiphenylsilyl)oxy]propyl]-1-(trimethylsilyl)cyclopropyl]-3,6,9-pentadecatrien-1-ol (Diastereomer G)

H. 1-[2-[3-[(t-Butyldiphenylsilyl)oxy]propyl-1-(trimethylsilyl)cyclopropyl]-3,6,9-pentadecatrien-1-ol (Diastereomer H)

and I. 1-[2-[3-[(t-Butyldiphenylsilyl)oxy]propyl]-1-(trimethylsilyl)cyclopropyl]-3,6,9-pentadecatrien-1-ol (Diastereomer I)

To a solution of 930 mg (1.90 mmol) of Part E protected alcohol in 5.0 ml of THF cooled to −78° was added 0.70 ml (2.6 m in hexane, 1.8 mmol) of n-butyllithium over several minutes. The reaction mixture was stirred at −78° for 2 hours, then a solution of 350 mg (1.59 mmol) of Part A aldehyde in 3.0 ml of ether was added dropwise. After 5 minutes the reaction was quenched with a small amount of methanol and then added to 20 ml of H₂O and extracted with two 10 ml portions of ether. The organic extracts were combined, dried (Na₂SO₄), concentrated in vacuo and the resulting crude oil purified by flash chromatography (15×5.0 cm, silica gel, 5:95 ether/petroleum ether containing 0.1% triethylamine) to afford 143 mg (14%) of title F diastereomer, 110 mg (11%) of title G diastereomer and 91 mg (9%) of a mixture of titles H and I diastereomers as pale yellow oils.

Title F diastereomer:

IR (film) 2.90(w), 3.40, 7.00, 8.03, 9.08, 12.02, 14.35 μ.

60 MHz $^1$H NMR(CDCl₃) δ 0.10 (s, 9H) 0.52–2.67 (m, 30H with 9H, singlet at δ 1.10), 2.87 (crude t, 4H), 3.13–3.52 (m, 1H); 3.78 (t, J=5 Hz, 2H), 5.10–5.77 (m, 6H), 7.23–7.93 (m, 10H).

MS (CI): 613 (MH⁺—H₂O), 463, 357, 285, 283, 203, 109. TLC: R_f (1:9 ether/petroleum ether)=0.60, PMA and UV.

Title G diastereomer:

60 MHz $^1$H NMR(CDCl₃) δ 0.10 (s, 9H), 0.53–2.50 (m, 30H with 9H singlet at δ 1.03), 2.80 (m, 4H), 3.37 (crude t, J=6 Hz, 1H), 3.70 (t, J=6 Hz, 2H), 5.03–5.77 (m, 6H), 7.17–7.87 (m, 10H).

TLC: R_f (1:9 ether/petroleum ether)=0.35, PMA and UV.

Title H and I diastereomers:

60 MHz $^1$H NMR(CDCl₃) δ 0.07, 0.18 (two singlets, total 9H) 0.50–2.23 (m, 30H with 9H, singlet at δ 1.07); 2.85 (m, 5H), 3.73 (t, J=6 Hz, 2H), 5.07–5.83 (m, 6H), b 7.20–7.90 (m, 10H).

MS (CI): 613 (MH⁺-$^H$₂O), 463, 357, 285, 283, 221, 203.

J.

(Z,Z,Z,Z)-2-(3,6,9-Pentadecatrienylidene)cyclopropane-propan-1-ol

To a solution of 140 mg (0.22 mmol) of Part F β-hydroxysilane in 2.0 ml of dry $CH_2Cl_2$ cooled to 0° was added 50 μl (0.36 mmol) of sieve-dried triethylamine followed by 22 μl (0.30 mmol) of thionyl chloride. The reaction mixture was stirred for 1.5 hours, then added to 10 ml of saturated aqueous $NaHCO_3$ solution and extracted with 10 ml of petroleum ether. The organic layer was separated, dried ($MgSO_4$) and concentrated in vacuo to give the crude β-chlorosilane as a yellow oil; TLC: $R_f$(1:9 ether/petroleum ether )=0.68, PMA and UV.

To a mixture of the crude β-chlorosilane derived from the Part F β-hydroxysilane in 2.5 ml of sieve-dried DMSO was added 0.75 ml (1.0M in THF, 0.75 mmol) of tetra-n-butylammonium fluoride solution. The dark reaction mixture was stirred at room temperature for 24 hours, then added to 15 ml of $H_2O$ and extracted with two 10 ml portions of petroleum ether. The organic extracts were combined, dried ($MgSO_4$), concentrated in vacuo and the resulting dark crude oil was purified by flash chromatography (15×3.0 cm, silica gel, 1:9 EtOAc/petroleum ether) to afford 27 mg (41%, two steps) of title alcohol as a pale yellow oil.

400 MHz $^1$H NMR($CDCl_3$) δ 0.72 (m, 1H) 0.89 (t, J=7 Hz, 3H), 1.14–1.50 (m, 3H), 1.57–1.76 (m, 10H), 2.05 (dt, J=7, 7 Hz, 2H), 2.82 (m, 4H), 2.95 (m, 2H), 3.69 (t, J=7 Hz, 3H), 5.29–5.53 (m, 6H), 5.69 (m, 1H).

67.5 MHz $^{13}$C NMR($CDCl_3$)δ 9.06, 14.1, 15.3, 22.6, 25.6, 27.2, 29.3, 30.2, 31.5, 32.5, 62.8, 116.7, 127.3 (weak), 127.6, 128.0, 128.1, 128.3, 128.5, 130.5.

MS (CI): 303 (MH+), 285, 263, 219, 217, 205, 203.

TLC: $R_f$(1:4 EtOAc/petroleum ether)=0.40, PMA.

K.

(Z,Z,Z,Z)-2-(3,6,9-Pentadecatrienylidene)cyclopropane-propanoic acid

To a solution of 32 mg (0.11 mmol) of Part J alcohol in 3.0 ml of acetone cooled to 0° was added 0.30 ml (0.7M in $H_2O$, 0.2 mmol) of Jones reagent. The reaction mixture was stirred for 2 hours, quenched with 0.25 ml of isopropyl alcohol, then warmed to room temperature and stirred for 15 minutes. The resulting green slurry was filtered through Celite/$MgSO_4$, the filtrate was concentrated in vacuo and the resulting crude oil purified by flash chromatography (12×3.0 cm, silica gel, 1:5 EtOAc/petroleum ether) to afford 30 mg (90%) of title product as a yellow oil.

IR (film), 3.41 (broad), 5.85, 6.96, 7.82, 8.25, 10.70, 14.06 μ. 400 MHz $^1$H NMR($CDCl_3$) δ 0.76 (m, 1H), 0.89 (t, J=7 Hz, 3H), 1.15–1.43 (m, 7H), 1.50 (m, 2H), 1.95 (m, 1H), 2.05 (dt, J=6,7 Hz, 2H), 2.47 (t, J=7 Hz, 2H), 2.80–2.90 (m, 4H), 2.94 (t, J=6 Hz, 2H), 5.30–5.53 (m, 6H), 5.71 (m, 1H).

67.5 MHz $^{13}$C NMR($CDCl_3$) δ 8.84, 14.0, 14.8, 22.6, 25.6, 27.2, 28.0, 29.3, 29.7, 30.1, 31.5, 33.6, 117.3, 126.4 (weak), 127.6, 127.9, 128.1, 128.3, 128.6, 130.5, 178.8 (weak).

MS(CI): 317(MH$^{30}$), 299, 257, 205, 203, 189, 177, 165, 151.

TLC: (1:5 EtOAc/petroleum ether) $R_f$=0.16, PMA.

EXAMPLE 2

[2E(3Z,6Z,9Z)]-2-(3,6,9-Pentadecatrienylidene)cyclopropanepropanoic acid

A.

[2E(3Z,6Z,9Z)]-2-(3,6,9-Pentadecatrienylidene)cyclopropane propan-1-ol

To a solution of 90 mg (0.14 mmol) of a mixture of Example 1 Parts H and I β-hydroxysilanes in 2.0 ml of dry $CH_2Cl_2$ cooled in an ice-bath was added 40 μl (0.29 mmol) of sieve-dried triethylamine followed by 18 μl (0.25 mmol) of thionyl chloride. The reaction mixture was stirred for 1 hour, then added to 10 ml of $H_2O$ and extracted with two 10 ml portions of petroleum ether. The combined organic extracts were dried ($MgSO_4$) and concentrated in vacuo to give the crude β-chlorosilane as a yellow oil.

TLC: $R_f$ (1:9 ether/petroleum ether)=0.71, PMA and UV.

To a mixture of the crude β-chlorosilane derived from the Example 1 Parts H and I β-hydroxysilanes in 2.0 ml of sieve-dried DMSO was added 0.45 ml (1.0M in THF, 0.45 mmol) of tetra-n-butylammonium fluoride solution. The dark reaction mixture was stirred at room temperature for 24 hours, then added to 15 ml of $H_2O$ and extracted with two 10 ml portions of petroleum ether. The combined organic extracts were dried ($MgSO_4$), concentrated in vacuo and purified by flash chromatography (15×3 cm, silica gel, 1:9 EtOAc/petroleum ether) to afford 10 mg (24% from Example 1 Parts H and I β-hydroxysilanes) of title alcohol as a pale yellow oil.

400 MHz $^1$H NMR($CDCl_3$) δ 0.71 (m, 1H), 0.90 (t, 3H), 1.15–1.55 (m, 10H), 1.63–1.75 (m, 2H), 2.07 (q, 2H), 2.81 (dd, J=6,6 Hz, 2H), 2.85 (dd, J=6,6 Hz, 2H), 2.94 (dd, J=7,7 Hz, 2H), 3.68 (t, 3H), 5.29–5. 44 (m, 5H), 5.50 (m, 1H), 5.76 (m, 1H).

67.5 MHz $^{13}$C NMR($CDCl_3$) δ 8.67, 14.1, 15.0, 22.6, 25.7 (strong), 27.3, 29.3, 29.5, 30.0, 31.6, 32.5, 62.7, 116.0, 127.6, 127.7 (weak), 128.1, 128.1, 128.5, 128.7 (weak), 130.5.

TLC: $R_f$(1:4 EtOAc/petroleum ether)=0.35, PMA. The $R_f$ of the Z-isomer was 0.40 under identical conditions.

B.

[2E(3Z,6Z,9Z)]-2-(3,6,9-Pentadecatrienylidene)cyclopropane propanoic acid

To a solution of 9.0 mg (0.30 mmol) of Part A alcohol in 1.5 ml of reagent acetone cooled in an ice-bath was added 0.12 ml (0.7M in $H_2O$, 0.08 mmol) of Jones reagent. The reaction mixture was stirred for 1.5 hours, quenched with 0.25 ml of isopropyl alcohol, warmed to room temperature and after 15 minutes, dried ($MgSO_4$). The resulting green slurry was filtered through Celite. The filtrate was concentrated in vacuo and the crude residual oil was purified by flash chromatography (12×3.0 cm, silica gel, 1:3 EtOAc/petroleum ether) to afford 8.0 mg (83%) of title acid as a yellow oil.

400 MHz $^1$H NMR($CDCl_3$) δ 0.75–0.82 (m, 1H), 0.90 (t, 3H), 1.20–1.50 (m), 1.57–1.82 (m, 3H), 2.05 (dt, J=7,7 Hz, 2H), 2.45 (t, J=7 Hz, 2H), 2.81 (dd, J=6,6 Hz, 2H), 2.85 (dd, J=6,6 Hz, 2H), 2.94 (dd, J=7,7 Hz, 2H), 5.28–5.45 (m, 5H), 5.46–5.53 (m, 1H), 5.79 (m, 1H).

67.5 MHz $^{13}$C NMR($CDCl_3$) δ 8.70, 14.1, 14.5, 22.6, 25.7, 27.3, 28.3, 29.3, 29.7, 29.9, 31.6, 33.5, 116.6, 126.6

(weak), 127.6, 128.0 (strong), 128.2, 128.5, 130.5, 178.0 (weak).

MS(CI): 317 (MH+), 299, 219, 203, 177, 165, 153.

TLC: Rhd f (1:3 EtOAc/petroleum ether)=0.18, PMA. The $R_f$ of the corresponding 2Z-isomer was 0.23 under identical conditions.

EXAMPLE 3

(Z,Z,Z,Z)-2-(3,6,9-Pentadecatrienylidene)cyclopropaneacetic acid

A. 1,1-Dibromo-2-vinylcyclopropane

To a slurry of 5.0 g (45 mmol) of potassium-t-butoxide in 50 ml (~570 mmol) of dry 1,3-butadiene cooled to −20° added dropwise a solution of 2.6 ml (30 mmol) bromoform in 5 ml of hexane over 15 minutes. The reaction mixture was stirred at −20° for 1 hour then at 0° for 1 hour followed by the addition 20 ml of ice-cold hexane and 20 ml of ice-cold H₂O. The resulting mixture was warmed slowly to temperature and stirred overnight to remove the excess butadiene. The residue was added to 20 ml of hexane, washed with two 25 ml portions of H₂O, dried (MgSO₄) and concentrated in vacuo to afford 6.20 g (91%) of title dibromide as a yellow liquid.

IR (neat) 2924 (weak), 1634, 1427, 1214, 1186, 1103, 1042, 1007, 980, 914, 714 cm$^{-1}$.

60 MHz $^1$H NMR(CDCl₃) δ 1.35–2.65 (m, 3H, cyclopropyl protons) 5.00–6.05 (m, 3H, vinyl protons)

B. 1-Bromo-1-trimethylsilyl-2-vinylcyclopropane

To a mechanically-stirred solution of 3.0 g (13.3 mmol) of Part A dibromide in 80 ml of 1:1 dry Et₂O/THF at −95° was added dropwise over 15 minutes, 5.8 ml (2.4M in hexane, 14 mmol) of n-butyllithium while maintaining the reaction temperature between −95° to −100°. The reaction was stirred at −95° to −100° for an additional 45 minutes, then 1.9 ml (15 mmol) of chlorotrimethylsilane was added over 5 minutes and stirring was continued at −95° for 1 hour then at −78° for 30 minutes. The resulting slurry was warmed at 0°, added to 150 ml of H₂O with 40 ml of ether. The organic extract was dried (MgSO₄) and carefully concentrated in vacuo (cold water bath) to afford 2.46 g (84%) of crude bromosilane as a yellow liquid.

IR (neat) 2915, 1664, 1247, 1100, 1027, 982, 903, 837 cm$^{-1}$.

60 MHz $^1$H NMR(CDCl₃) δ 0.08–0.15 (overlapping s, 9H, —SiMe₃) 1.00–1.75 (m, ~3H, cyclopropyl) 2.05–2.57 (m, ~1H, allylic) 4,90–5.63 (m, 3H, vinyl)

MS(CI): 221, 219 (M+H)+

C. 1-Bromo-2-ethan-2-ol-1-trimethylsilylcyclopropane

To a solution of 2.15 g (9.82 mmol) of crude Part B bromosilane in 5.0 ml of dry THF cooled to 0° was added dropwise 4.0 ml (1.0M in THF, 4.0 mmol) of borane-tetrahydrofuran complex. The reaction mixture was warmed to room temperature, stirred for 2.5 hours then re-cooled to 0°. To the cooled solution was added slowly 2 ml of 3M aqueous NaOH solution, then 2 ml of 30% aqueous H₂O₂. The resulting mixture was warmed to room temperature, then to 55° for 1 hour, followed by addition to 50 ml of 1M aqueous NaOH and extraction with two 25 ml portions of ether. The combined organic extracts were dried (MgSO₄) and concentrated in vacuo to give a yellow oil. The crude material was purified by flash chromatography (silica gel, 15×5.0 cm, 1:5 EtOAc/petroleum ether) to afford 1.63 g (70%) of title alcohol as a pale yellow oil.

IR (neat) 3145, 2907, 1420, 1046, 837 cm$^{-1}$.

60 MHz $^1$H NMR (CDCl₃) δ 0.05, 0.17 (overlapping s, 9H, -SiMe3) 0.57–2.10 (m, 6H) 3.70, 3.73 (overlapping t, J=6, 2H, -CH₂-OH)

TLC: $R_f$ (silica gel, 1:1 EtOAc/petroleum ether)=0.71, PMA.

D. 2-Bromo-2-(trimethylsilyl)cyclopropaneethanol

To a solution of 1.40 g (5.91 mmol) of Part C alcohol, 1.59 g (5.80 mmol) of t-butylchlorodiphenylsilane, 1.25 ml (8.9 mmol) of triethylamine in 10 ml of dry CH₂Cl₂ cooled in an ice-bath was added 30 mg (0.25mmol) of 4-dimethylaminopyridine. The reaction mixture was warmed to room temperature, then after 6hours added to 25 ml of ice-cold 1M aqueous HCl solution and acted with 25 ml of ether. The organic extract was dried (MgSO₄) and concentrated in vacuo to give an oil. The crude material was purified by flash chromatography (silica gel, 16×5.0 cm, 1:9 CH₂Cl₂/petroleum ether) to afford 2.56 g (93%) of protected alcohol a a clear, colorless oil.

IR neat) 2907, 1425, 1248,1106, 838, 735, 699 cm$^{-1}$.

60 MHz $^1$H NMR (CDCl₃) δ 0.07, 0.15 (overlapping s, total 9H, -SiMe₃) 0.55–2.18 (m with t-butyl s at 1.08, 14H) 3.75, 3.82 (overlapping t, J=6, 2H, —CH₂—OSi) 7.18–8.00 (m, 10H, aromatic).

TLC: $R_f$ (silica gel, 1:5 CH₂Cl₂/petroleum ether)=0.44, UV and PMA.

E. 1 -[2-[2-(t-Butyldiphenylsilyl)oxy]ethyl]-1-(trimethylsilyl)cyclopropyl]-3,6,9-pentadecatrien-1-ol (Isomer E) and

F. 1-[2-[2-(t-Butyldiphenylsilyl)oxy]ethyl]-1-(trimethylsilyl)cyclopropyl]-3,6,9-pentadecatrien-1-ol (Isomer F)

To a solution of 820 (1.73 mmol) of Part D protected alcohol in 4.0 dry THF cooled to −78° was added 0.70 ml (2.4 hexane 1.7 mmol) of n-butyllithium, then after 2 hours a solution of 300 mg (1.36 mmol) of (Z,Z,Z)-3,6,9-pentadecatrienal (prepared as described in Example 1 Part A) in 2 ml of THF was added. The reaction mixture was stirred for 5 minutes at −78° , quenched with a small amount of methanol, added to 20 ml of H₂O and extracted with two 15 ml of petroleum ether. The organic extracts combined, dried (Na₂SO₄) and concentrated in vacuo to give a colorless oil. The crude material was purified by flash chromatography (silica gel, 20×5.0 cm. 1:19 ether/petroleum ether containing 0.1% Et₃N) to afford 205 mg (24%) of title E isomer ($R_f$ 0.45, 1:9 ether/petroleum ether, PMA) and 55 mg (7%) of title F isomer ($R_f$=0.19, 1:9 ether/petroleum ether, PMA) as oils.

G. (Z,Z,Z,Z)-2-(3,6,9-Pentadecatrienylidene)cyclopropane ethan-1-ol

To a solution of 200 mg (0.32 mmol) of Part E β-hydroxysilane and 80 μl (0.57 mmol) of sieve-dried triethylamine in 3.0 ml of dry CH₂Cl₂ at 0° was added 36 μl (0.50 mmol) of thionyl chloride. The reaction mixture was stirred for 30 minutes, then added to 10 ml of H₂O and extracted with 15 ml of petroleum ether. The organic extract was dried (MgSO₄) and concentrated in vacuo to afford the corresponding β-chlorosilane as a yellow oil. The crude β-chlorosilane was stirred with 1.0 ml (1.0M in THF, 1.0 mmol) of tetra-n-butylammonium fluoride solution in 3.0 ml of sieve-dried DMSO at room temperature for 36 hours. The resulting dark solution was added to 20 ml of H₂O and extracted with 15 ml of petroleum ether. The organic layer was washed with an additional 20 ml of H₂O, dried (MgSO₄) and concentrated in vacuo to give a dark oil. The crude material was purified by flash chromatography (silica gel, 15×3.0 cm, 1:9 EtOAc/petroleum ether) to afford 40 mg (44%) of isomerically pure title alcohol as a pale yellow oil.

IR (neat) 3226, 2882, 1658, 1445, 1050 cm$^{-1}$

Partial 400 MHz $^1$H NMR (CDCl₃) δ 0.79 (m, 1H, cyclopropyl) 2.81 (dd, J=6,6, 2H, doubly allylic —CH₂—) 2.85 (dd, J=6,6, 2H, doubly allylic —CH₂—) 2.96 (crude dd, 2H, doubly allylic —CH₂, C₇) 5.28–5.54 (m, 6H, olefinic) 5.72 (m, 1H, olefinic - methylene cyclopropane)

MS (CI): 289 (M+H)$^+$

TLC: $R_f$ (silica gel, 1:4 EtOAc/petroleum ether)=0.37, PMA. The $R_f$ of the corresponding E-isomer was 0.32 under identical conditions. TLC showed the absence of the E-isomer.

H.
(Z,Z,Z,Z)-2-(3,6,9-Pentadecatrienylidene)cyclopropaneacetic acid

To a solution of 37 mg (0.13 mmol) of Part G alcohol in 3 ml of acetone cooled to 0° was added 0.20 ml of Jones reagent (Fieser & Fieser, Vol. I, p. 142). The reaction mixture was stirred for 30 minutes, quenched with several drops of isopropyl alcohol and the resulting green slurry filtered through Celite. The filtrate was concentrated to give an oil. The crude material was purified by flash chromatography (silica gel, 6×3 cm, 1:15 EtOAc/petroleum ether) to afford 23 mg (59%) of title product as a pale yellow oil.

Partial 400 MHz $^1$H NMR (CDCl₃) δ 1.78 (m, 1H, cyclopropyl —CH—) 2.05 (dt, J=7,7, 2H, allylic —CH₂—) 2.23 (dd, J=8,16, 1H, —CH₂—CO₂H) 2.58 (dd, J=6,16, 1H, —CH₂—CO₂H) 2.81 (m, 4H, doubly allylic —CH₂—, C₁₀ and C₁₃) 2.95 (m, 2H, doubly allylic —CH₂—, C₇) 5.25–5.55 (m, 6H, olefinic) 5.77 (m, 1H, olefinic - methylene cyclopropane)

MS (CI): 303 (M+H)$^+$

TLC: $R_f$ (silica gel, 1:1 EtOAc/petroleum ether)=0.51, PMA. The $R_f$ of the corresponding E-isomer was 0.44 under identical conditions.

EXAMPLE 4
(E,Z,Z,Z)-2-(3,6,9-Pentadecatrienylidene)cyclopropaneacetic acid

A.
(E,Z,Z,Z)-2-(3,6,9-Pentadecatrienylidene)cyclopropane ethan-1-ol

To a solution of 50 mg (0.081 mmol) of Example 1 Parts H and I β-hydroxysilane isomers and 20 μl (0.14 mmol) of sieve-dried triethylamine in 20 ml of dry CH₂Cl₂ cooled to 0° was added 10 μl (0.14 mmol) of thionyl chloride. The reaction mixture was stirred for 1 hour then added to 10 ml of H₂O and extracted with 10 ml of petroleum ether. The organic extract was dried (MgSO₄) and concentrated in vacuo to give the corresponding β-chlorosilane as a yellow oil.

A solution of the crude β-chlorosilane (≦0.081 mmol) and 0.24 ml (1.0M in THF, 0.24 mmol) of tetra-n-butylammonium fluoride in 1.0 ml of sieve-dried DMSO was stirred at room temperature for 24 hours.

The resulting dark reaction mixture was added to 10 ml of H₂O and extracted with 10 ml of petroleum ether. The organic extract was dried (MgSO₄), concentrated in vacuo and the resulting dark oil purified by flash chromatography (silica gel, 15×1.5 cm, 1:12 EtOAc/petroleum ether) to afford 8.0 mg (35%) of title alcohol as a yellow oil.

TLC: $R_f$ (silica gel, 1:4 EtOAc/petroleum ether)=0.32, PMA, single spot. The $R_f$ of the corresponding Z-isomer under identical conditions was 0.37.

B.
(E,Z,Z,Z)-2-(3,6,9-Pentadecatrienylidene)cyclopropaneacetic acid

To a solution of 8.0 mg (0.028 mmol) of Part A alcohol in 2.0 ml of reagent acetone cooled to 0° was added 2 drops of Jones reagent (Fieser and Fieser, Vol. I, p. 142). The reaction mixture was stirred for 30 minutes, quenched with several drops of isopropyl alcohol and the resulting green slurry filtered through Celite. The filtrate was concentrated in vacuo and the residue purified by flash chromatography (silica gel, 8.0×1.0 cm, 1:2 EtOAc/petroleum ether (to afford 6.0 mg (71%) of title acid product as a pale yellow oil.

Partial 400 MHz $^1$H NMR (CDCl₃) δ 1.70 (m, 1H, cyclopropyl) 2.05 (dt J=7,7, 2H, allylic —CH₂—) 2.37 (d, J=7,1 H—CH₂CO₂H) 2.38 (d, J=7, 1H, —CH₂CO₂H) 2.82 (m, 4H, doubly allylic —CH₂—, C₁₀ and C₁₃) 2.95 (dd, J=7,7, 2H, doubly allylic —CH₂—, C₇) 5.30–5.55 (m, 6H, olefinic) 5.88 (m, 1H, olefinic-methylene cyclopropane)

MS (CI): 303 (M+H)$^+$

TLC: $R_f$ (silica gel, 1:1 EtOAc/petroleum ether)=0.44, PMA. The $R_f$ of the corresponding Z-isomer under identical conditions was 0.51.

What is claimed is:

1. A compound having the structure

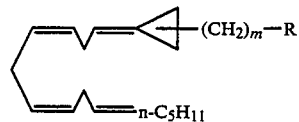

wherein R is CH₂OH or CO₂H and m is 1 or 2.

2. The compound as defined in claim 1 wherein R is CH₂OH.

3. The compound as defined in claim 1 wherein R is CO₂H.

4. The compound as defined in claim 1 having the structure.

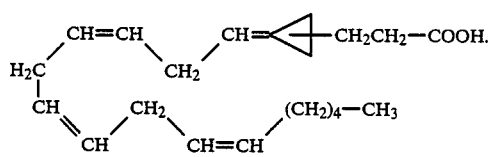

5. The compound as defined in claim 1 having the structure

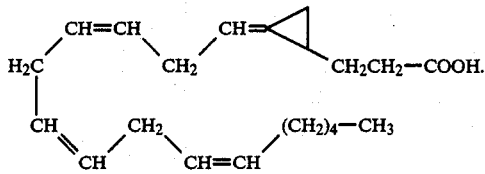

6. The compound as defined in claim 1 having the structure.

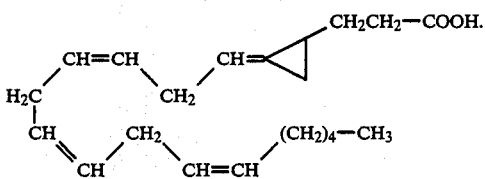

7. The compound as defined in claim 1 having the structure

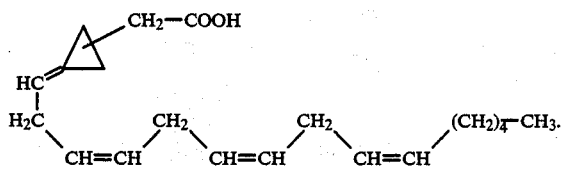

8. The compound as defined in claim 1 having the structure

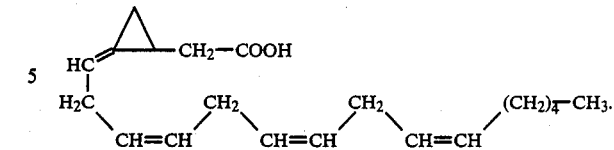

9. The compound as defined in claim 1 having the structure

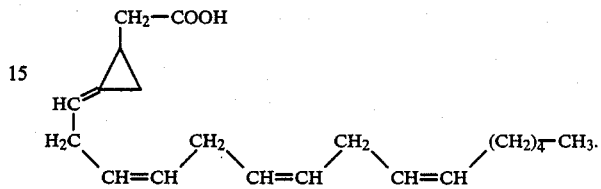

10. A composition for inhibiting allergic conditions in a mammalian species, comprising an effective amount of a compound as defined in claim 1 or a pharmaceutically acceptable salt thereof, and a pharmaceutically acceptable carrier thereof.

11. A method of inhibiting leukotriene and prostaglandin biosyntheses, which comprises administering to the circulatory system of a mammalian host an effective amount of a compound as defined in claim 1 or a pharmaceutically acceptable salt thereof.

12. The method as defined in claim 11 wherein said compound is administered in an amount within the range of from about 1 to about 100 mg/kg.

13. A method for treating asthma in a mammalian species in need of such treatment, which comprises administering to a mammalian host an effective amount of a compound as defined in claim 1 or a pharmaceutically acceptable salt thereof.

14. A method for treating inflammation in a mammalian species in need of such treatment, which comprises administering to a mammalian host an effective amount of a compound as defined in claim 1 or a pharmaceutically acceptable salt thereof.

* * * * *